United States Patent [19]

Ross et al.

[11] Patent Number: 5,610,002
[45] Date of Patent: Mar. 11, 1997

[54] PHOTOGRAPHIC COMPOSITION CONTAINING A THICKENING AGENT

[75] Inventors: Robert J. Ross, Rochester; Pranab Bagchi, Webster; Richard W. Connelly, Rochester, all of N.Y.

[73] Assignee: Eastman Kodak Company, Rochester, N.Y.

[21] Appl. No.: 558,974

[22] Filed: Nov. 13, 1995

Related U.S. Application Data

[63] Continuation of Ser. No. 264,552, Jun. 23, 1994, abandoned, which is a continuation-in-part of Ser. No. 975,238, Nov. 12, 1992, abandoned.

[51] Int. Cl.[6] .................................................. G03C 1/047
[52] U.S. Cl. .................. 430/54.6; 430/634; 430/635; 430/636; 430/642
[58] Field of Search ................................ 430/546, 634, 430/635, 636, 642; 106/125, 131, 135, 136; 252/354, 356

[56] References Cited

U.S. PATENT DOCUMENTS

| | | | |
|---|---|---|---|
| 2,257,267 | 10/1950 | Hart et al. | |
| 2,681,294 | 6/1954 | Beguin. | |
| 2,761,417 | 9/1956 | Russell et al. | |
| 3,184,312 | 5/1965 | Gates et al. | |
| 3,535,353 | 10/1970 | Kamal et al. | 103/30 |
| 3,632,374 | 1/1972 | Greiller | 430/538 |
| 3,860,425 | 1/1975 | Ono et al. | |
| 3,861,924 | 1/1975 | Mackey et al. | |
| 3,912,517 | 10/1975 | VanPoucke et al. | |
| 3,926,869 | 12/1975 | Horie et al. | 260/8 |
| 4,370,412 | 1/1983 | Cruikshank et al. | 430/635 |
| 4,410,624 | 10/1983 | Plaschnick et al. | 430/546 |
| 4,525,392 | 6/1985 | Ishizaki et al. | 427/420 |
| 4,569,863 | 2/1986 | Koepke et al. | 427/402 |
| 4,797,349 | 1/1989 | Takahashi et al. | 430/636 |
| 4,920,004 | 4/1990 | Bagchi | 428/407 |
| 4,939,077 | 7/1990 | Helling et al. | 430/527 |
| 5,013,640 | 5/1991 | Bagchi et al. | 430/546 |
| 5,026,632 | 6/1991 | Bagchi et al. | 430/545 |
| 5,055,379 | 10/1991 | Bagchi et al. | 430/289 |
| 5,087,554 | 2/1992 | Chari et al. | 430/546 |
| 5,153,112 | 10/1992 | Yoshida et al. | 430/636 |

FOREIGN PATENT DOCUMENTS

| | | | |
|---|---|---|---|
| 358073 | 3/1990 | European Pat. Off. | |
| 367572 | 5/1990 | European Pat. Off. | |
| 2150505 | 4/1973 | France | G01C 7/00 |
| 2000926 | 7/1971 | Germany | 430/642 |
| 857-917 | 8/1981 | U.S.S.R. | G03I 1/06 |
| 91/14967 | 10/1991 | WIPO. | |

OTHER PUBLICATIONS

Takahashi et al. U.S. Statutory Invention Registration H706 (Nov. 7, 1989).

*Primary Examiner*—Janet C. Baxter
*Attorney, Agent, or Firm*—Andrew J. Anderson

[57] ABSTRACT

This invention describes gelatin thickening compounds for photographic coating melts with the general structure:

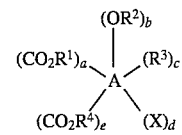

wherein:

A is an aromatic or heteroaromatic group;

X is $SO_3M$ or $CO_2M$

M is H or an alkali metal, ammonium or pyridinium ion; each R1 and R2 is independently an alkyl or substituted alkyl group, each alkyl group being straight or branched chain and having 1 to 30 carbon atoms;

each R3 and R4 is independently H or an alkyl or substituted alkyl group, each alkyl group being straight or branched chain and having 1 to 30 carbon atoms;

each of a, b, c and e is independently 0, 1, 2 or 3, with the proviso that $a+b+c+e$ is at least 1; and d is 1, 2, or 3;
with the further proviso that when A is phenyl, X is $SO_3M$, d is 1 and any one of a, c, or e is 1, the sum of $a+b+c+e$ is at least 2; and wherein there is a substantial absence of a compound containing one or more $-SO_2^-$ groups in the composition.

18 Claims, 5 Drawing Sheets

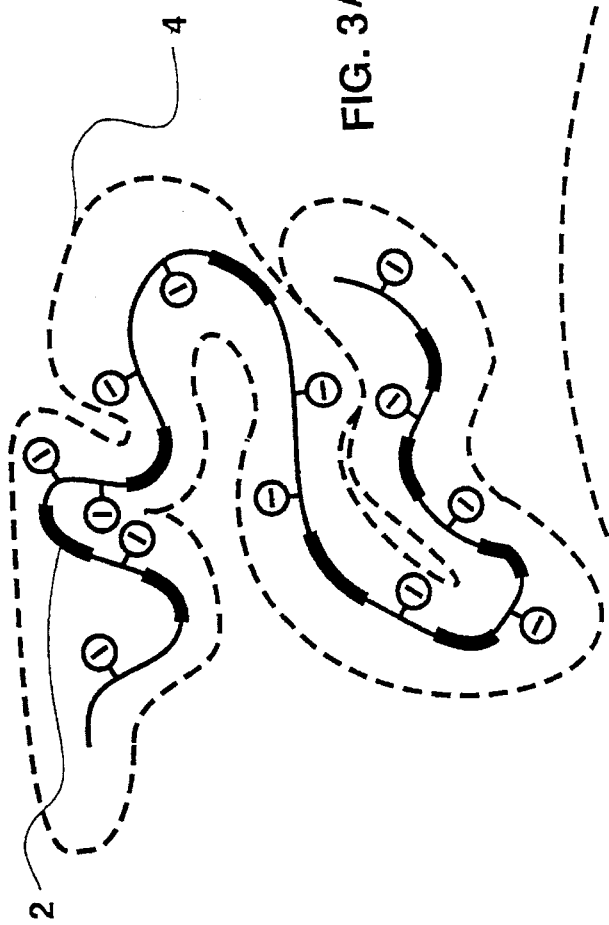
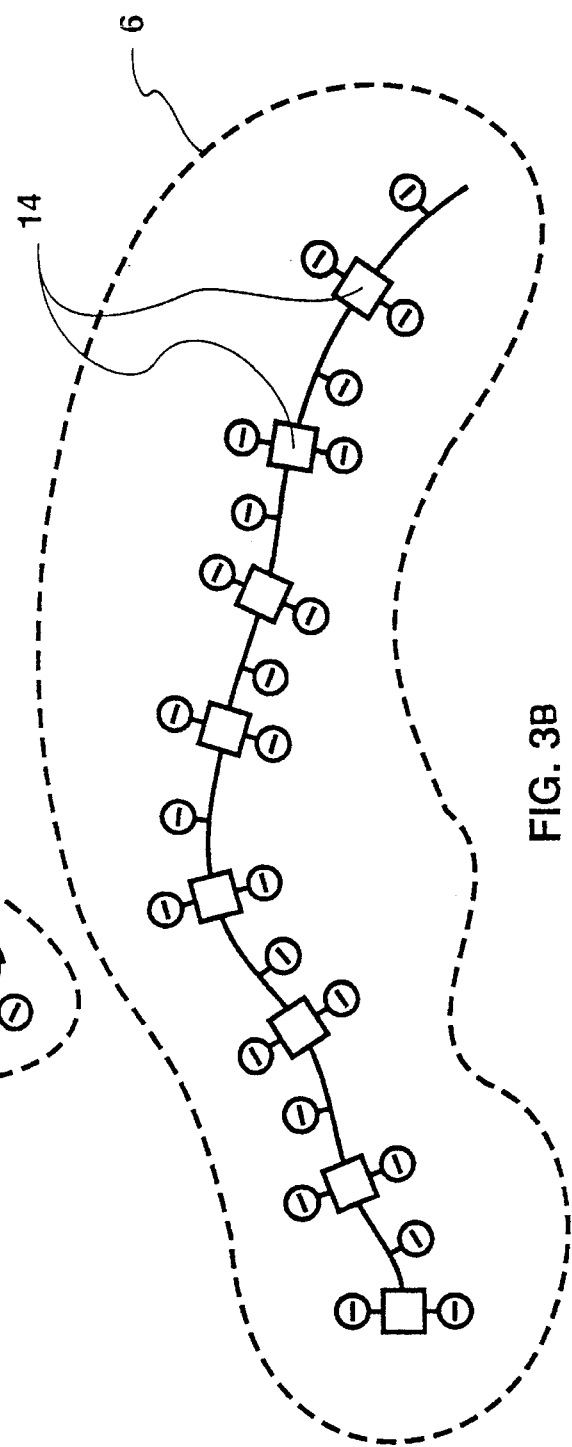
FIG. 3A
FIG. 3B

PHOTOGRAPHIC COMPOSITION CONTAINING A THICKENING AGENT

This application is a continuation of application Ser. No. 08/264,552, filed 23 Jun. 1994, now abandoned, which is a continuation in part of application Ser. No. 07/975,238 filed Nov. 12, 1992, now abandoned, the entire disclosure of which is incorporated herein by reference.

FIELD OF THE INVENTION

This invention relates to a photographic composition containing a thickening agent, to a process for preparing said composition, to a photographic element prepared therefrom, to a method of preparing said photographic element, and to a novel compound useful as a thickening agent in photographic compositions.

BACKGROUND OF THE INVENTION

Photographic elements typically comprise a plurality of photosensitive layers and non-photosensitive layers, such as, interlayers, anti-halation layers, protective layers and the like. The layers generally are coated from fluid solutions containing a hydrophilic colloid, such as gelatin. Usually, coating takes place at temperatures between about 35° to about 50° C. The fluid solutions are frequently referred to as "melts" or "coating melts".

Generally, in the photographic art there are two primary methods of coating photographic compositions. One is the bead coating process. U.S. Pat. No. 2,761,417 to Russell et al., U.S. Pat. No. 2,681,294 to Beguin, and U.S. Pat. No. 4,525,392 to Ishizaki illustrate simultaneously applying multiple layers of photographic compositions by bead coating processes, and apparatus for practicing those processes.

The second primary method is the curtain coating process. U.S. Pat. No. 3,632,374 to Greiller, and U.S. Pat. No. 4,569,863 to Koepke et al., illustrate apparatus and processes for curtain coating.

It is well known that adjustment and control of viscosities of typical photographic coating melts of individual layers can improve uniformity of layer thickness of the coated product. It is also known that layer viscosities outside optimum ranges may cause undesired variations in layer thicknesses during flow on the slides of the coating hopper or on a non-horizontal web path after coating.

Coating melts with low gelatin concentrations, below about 4% gelatin, have relatively low viscosities and as a result are particularly difficult to coat in multilayer slide hopper coating machines without undesired variation in layer thickness. Usually, in multilayer curtain coating devices even higher viscosities are desirable for producing uniform coatings.

There are certain advantages, however, in using low gelatin-containing melts. In general, the lower the gelatin content, the thinner the resulting coating. Thinner layers in photographic coatings provide the advantages of (1) sharper images, and (2) faster processing films.

It has been proposed to incorporate polymeric materials into gelatin-containing photographic coating compositions to increase the viscosity thereof. See for example U.S. Pat. Nos. 3,861,924 to Mackey et at and 3,926,869 to Horie et al and Soviet patent publication SU 857,917 to Korneva. However, the use of polymeric materials can add to the cost of the product as polymers with sufficient purity and specific molecular weight or molecular weight distribution for photographic use are expensive to manufacture.

Therefore, there is a need to control the viscosity of gelatin-containing photographic melts in a cost effective manner and in particular to formulate high viscosity, low gelatin-containing photographic melts that are suitable for producing relatively thin, uniform multilayer product coatings, especially in multiple layer slide hopper or curtain coating machines.

SUMMARY OF THE INVENTION

One aspect of the invention comprises a photographic composition comprising an aqueous medium containing a hydrophilic colloid and a compound of the formula:

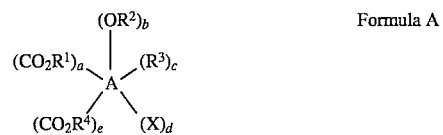

Formula A wherein:
A is an aromatic or heteroaromatic group;
X is $SO_3M$ or $CO_2M$
M is H or an alkali metal, ammonium or pyridinium ion;
each $R^1$, $R^2$, and $R^3$ is independently an alkyl or substituted alkyl group, each alkyl group being straight or branched chain and having 1 to 30 carbon atoms;
$R^4$ is H or an alkyl or substituted alkyl group, each alkyl group being straight or branched chain and having 1 to 30 carbon atoms;
each of a, b, c and e is independently 0, 1, 2 or 3, with the proviso that a+b+c+e is at least 1; and
d is 1, 2, or 3;
with the proviso that when A is phenyl, X is $SO_3M$, d is 1 and any one of a, c, or e is 1, the sum of a+b+c+e is at least 2; and wherein there is a substantial absence of a compound containing one or more $—SO_2^-$ groups in the composition.

Another aspect of this invention comprises a method of thickening a photographic composition comprising an aqueous medium containing a hydrophilic colloid, which method comprises adding thereto a compound of Formula A.

A further aspect of this invention comprises a multilayer photographic element comprising at least one layer formed from a photographic composition comprising an aqueous medium containing a hydrophilic colloid and a compound of Formula A.

Yet another aspect of this invention comprises a method of preparing a multilayer photographic element which comprises applying to a support a plurality of photographic layers, at least one of said layers being formed from a photographic composition comprising an aqueous medium containing a hydrophilic colloid and a compound of Formula A.

A still further aspect of this invention is a novel compound of the formula:

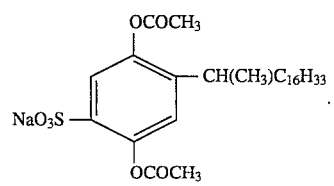

ADVANTAGEOUS EFFECT OF THE INVENTION

This invention provides a thickening agent for photographic compositions which permit melts of the composition to be applied as a substantially uniform layer to a support using conventional coating equipment. The thickening agent increases the viscosity of coating melts of the composition permitting control of the viscosity by adding an appropriate amount of the thickening agent. If the gelatin content of the photographic composition is low, a comparatively thin uniform layer can be achieved, thus providing sharper images and faster processing times.

BRIEF DESCRIPTION OF THE DRAWINGS

FIG. 3a and FIG. 3b illustrate attachment of multiple thickening agent molecules to a gelatin molecule.

DETAILED DESCRIPTION OF THE INVENTION

Figure 1:
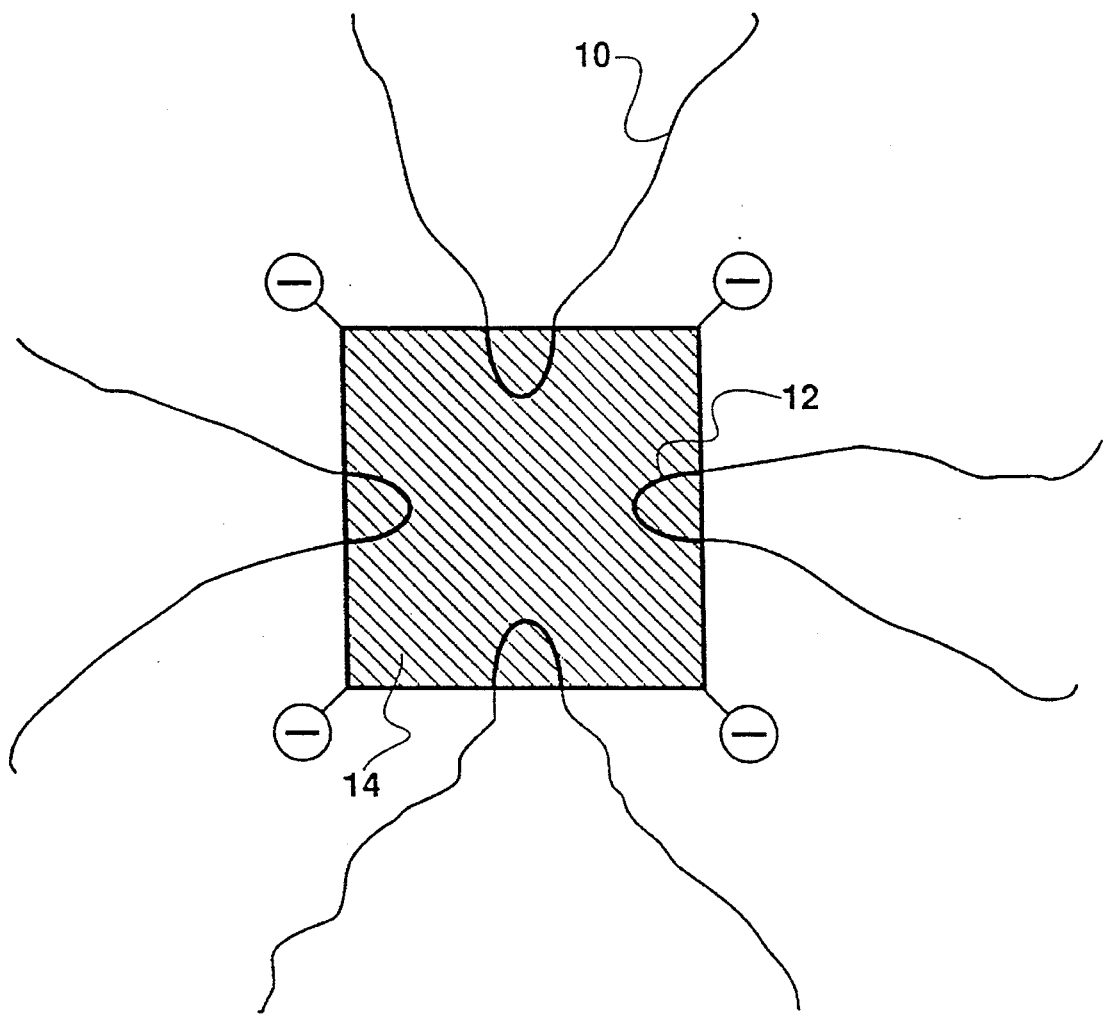
FIG. 1. illustrates attachment of multiple gelatin molecules to a compound used as a thickening agent in accordance with this invention.

The photographic composition of this invention comprises an aqueous medium containing a hydrophilic colloid, preferably gelatin. The composition may contain gelatin of any kind such as lime processed ossein, acid processed ossein, pig skin gelatin or derivatized gelatins as described by Bagchi (U.S. Pat. No. 4,920,004; U.S. Pat. No. 5,026,632; U.S. Pat. No. 5,055,379; and U.S. Pat. No. 5,013,640).

The composition of this invention may contain conventional photographic agents such as silver halide emulsions, coupler dispersions, dispersions of other photographic agents, synthetic polymers, and soluble chemicals such as oxidized developer scavengers, dyes, optical brighteners, masking couplers, surfactants, and the like. A summary of photographic addenda which can be incorporated into the aqueous media can be found in Research Disclosure 308,119 dated December 1989, the disclosure of which is incorporated herein by reference.

The amount of hydrophilic colloid present in the composition of this invention is about 3 to about 20% by weight, based on the weight of the composition. As mentioned above, the invention has particular utility preparing thickened photographic melts in which the hydrophilic colloid content is less than about 4%. Percentages reported in this patent application are by weight, based on the total weight of the composition, unless otherwise specified. The hydrophilic colloid is preferably gelatin.

The thickening agent utilized in accordance with this invention is an organic chemical compound that is photographically inert and has large hydrophobic groups and one or more anionic groups such as $-SO_3^-$ (i.e., sulfonate) groups or carboxy groups in the molecule. Such compounds are generally soluble to the extent of at least about 5%, by weight, in water, gelatin-containing aqueous media, or a solution of water containing about 5 to about 20%, by weight, of a water miscible auxiliary solvent such as methanol, ethanol, propanol, isopropanol, acetone, methyl ethyl ketone, ethyl acetate, or the like. The thickening agent used in accordance with this invention should not form an insoluble complex with the hydrophilic colloid since precipitation of such a complex would be undesirable. The thickening agent should not contain reactive groups, such as $-SO_2^-$ groups. Further, it is preferred that there is a substantial absence of compounds containing $-SO_2^-$ groups in the composition.

The thickening agent utilized in this invention can be represented by the general structural formula:

$$(CO_2R^1)_a \underset{(CO_2R^4)_e}{\overset{(OR^2)_b}{\underset{}{A}}} \overset{(R^3)_c}{\underset{(X)_d}{}} \quad \text{Formula A}$$

wherein:
A is an aromatic or heteroaromatic group;
X is $SO_3M$ or $CO_2M$
M is H or an alkali metal, ammonium or pyridinium ion;
each $R^1$, $R^2$, and $R^3$ is independently an alkyl or substituted alkyl group, each alkyl group being straight or branched chain and having 1 to 30 carbon atoms;
$R^4$ is H or an alkyl or substituted alkyl group, each alkyl group being straight or branched chain and having 1 to 30 carbon atoms;
each of a, b, c and e is independently 0, 1, 2 or 3, with the proviso that a+b+c+e is at least 1; and
d is 1, 2, or 3;
with the further proviso that when A is phenyl, X is $SO_3M$, d is 1 and any one of a, c, or e is 1, the sum of a+b+c+e is at least 2; and wherein there is a substantial absence of a compound containing one or more $-SO_2^-$ groups in the composition.

The use of anionic compounds containing a hydrophobic group as surfactants in photographic compositions is known. See for example U.S. Pat. Nos. 3,860,425 to Ono et al and 3,912,517 to Van Poucke et al.

Preferred compounds of Formula A are those in which A is phenyl, X is $SO_3M$, M is H, or a sodium, potassium, pyridium, or ammonium ion, $R^3$ is a straight or branched chain alkyl group having 1 to 30 carbon atoms, $R^4$ is a straight or branched chain alkyl group having 1 to 30 carbon atoms, d is 1, c is 1, e is 2 or 3 and a and b are each 0 in accordance with the following formula:

$$\underset{(CO_2R^4)_e}{\overset{}{\underset{}{A}}} \overset{(R^3)_c}{\underset{(X)_d}{}}$$

Particularly preferred is the compound of structure No. 1 set forth below.

The compounds used as thickening agents in accordance with this invention are generally known compounds and can be prepared by known methods. The compound of structure No. 1, below, is novel and a method for preparing this compound is set forth in the preparative example below.

Examples of compounds of compounds useful as thickening agents in accordance with this invention include, but are not limited to, compounds of the following structures:

No. 1:

[Structure showing a benzene ring with $NaO_3S$, two $OCOCH_3$ groups, and $CH(CH_3)C_{16}H_{33}$ substituents]

No. 2:
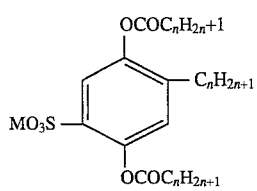
No. 3:
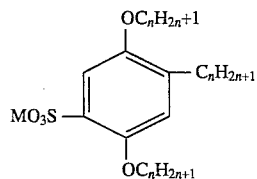
No. 4:
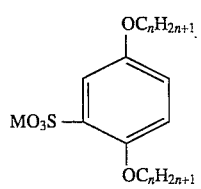
No. 5:
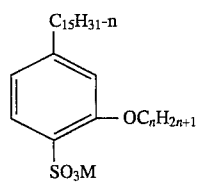
No. 6:
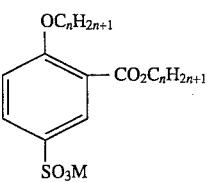
No. 7:
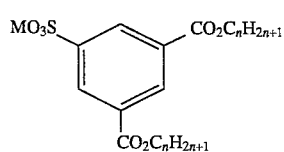
No. 8:
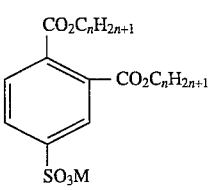
No. 9:
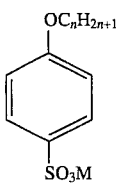
No. 10:
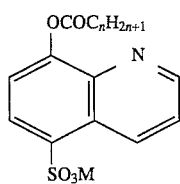
No. 11:
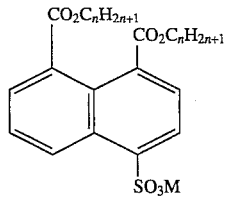
No. 12:
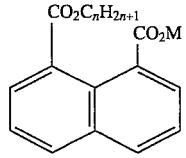
No. 13:
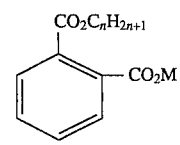
No. 14:
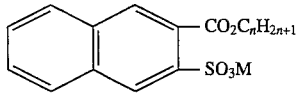
No. 15:
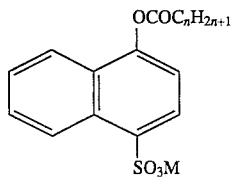
No. 16:
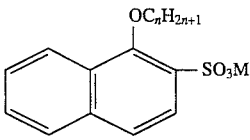

No. 17:
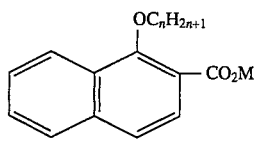
No. 18:
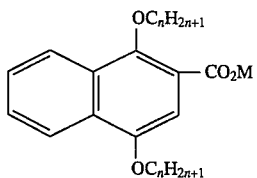
No. 19:
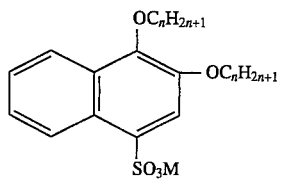
No. 20:
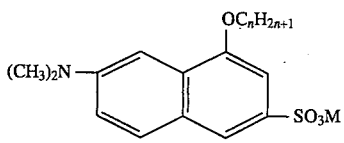
No. 21:
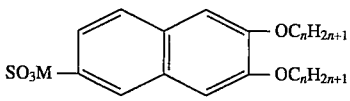
No. 22:
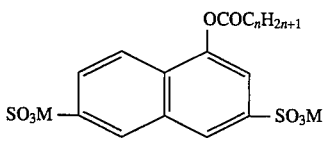
No. 23:
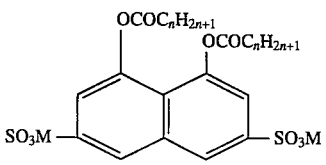
No. 24:
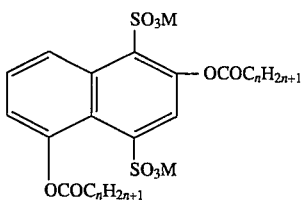
No. 25:
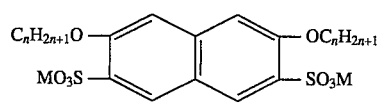
No. 26:
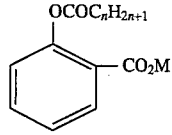
No. 27:
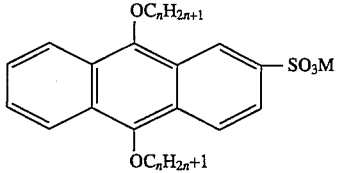
No. 28:
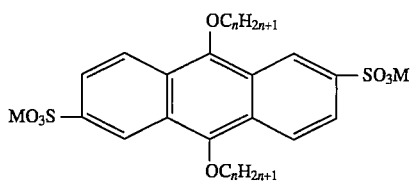
No. 29:
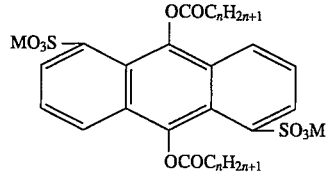
No. 30:
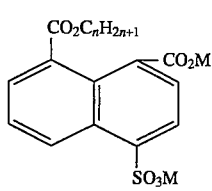
No. 31:
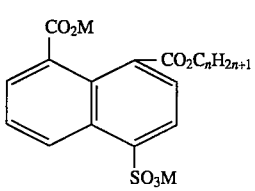
No. 32:
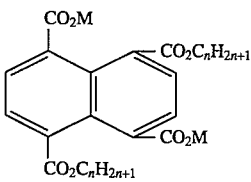

-continued

No. 33:

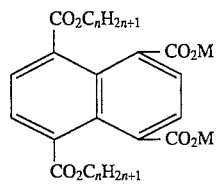

No. 34:

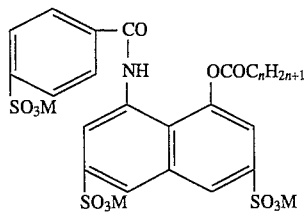

No. 35:

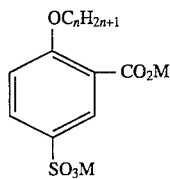

In structures 2 through 35 each n is between 1 to about 18, with the total number of alkyl carbon atoms preferably being between about 8 to about 30; M is H, or an alkali metal, pyridinium, or ammonium ion, preferably Na, K, or pyridinium.

In a preferred embodiment of the invention, a compound of Formula A is added to a gelatin containing photographic composition to thicken the composition when it is in the molten state. The resulting thickened melt is used to coat a layer of the composition onto a photographic support. The composition may be the only photographic layer coated on the support, but preferably is one of a plurality layers coated onto the support. More preferably, compositions of this invention are used for at least two of the individual layers of a multilayer photographic coating applied to a support.

Viscosity requirements for individual melts in multilayer coatings depend on the method and equipment (e.g. bead or curtain coatings) used for the coating process and upon many other considerations. Therefore, the ideal viscosity for any coating melt is in a small range that is most desirable for particular coating machine and melt composition. This invention provides a means for the enhancement of viscosity of a photographic melt to a given value that is ideal for a particular coating process and equipment. For this purpose, the lowest viscosity needed to be attained may lie anywhere between about 3 to 200 cP (mP*s) at low shear rate (less than 100 sec$^{-1}$). A preferred range is above about 5 cP (mP*s).

While in preferred embodiments of the invention the composition has a low gelatin content, it is to be understood that melts of photographic compositions of any desired gelatin content can be thickened in accordance with this invention.

As mentioned above, producing multilayer products using thickened photographic melts of this invention provide substantially defect free multilayer coatings. The term "substantially defect free multilayer coatings" means coatings that contain few, if any, observable or measurable layer thickness variations or other nonuniformity in the individual layers of the multilayer product coatings. The extent of nonuniformity which is acceptable depends on the type of photographic coating, the end product and its usage.

The coating melts of this invention are suitable mainly for multilayer coating machines using a multiple slide hopper or by the method of curtain coating.

The photographic products prepared in accordance with this invention may be a color paper product, color negative product, color transparency product, black-and-white paper, or film products, etc. as described in Research Disclosure, issue 308,119 pp. 993 to 1015, December 1989, the disclosure of which is incorporated herein by reference.

A preferred embodiment this invention is directed to a melt for the coating of a layer in a photographic element and which contains gelatin and an anionically charged, hydrophobic group containing compound that is (a) water soluble or rendered water soluble by solvent assistance, and (b) which confers a desirably high viscosity on gelatin melts.

It is preferred that the coating melts have a composition such as set forth in the following table:

| Coating Melts of the Invention | | |
|---|---|---|
| | Composition (weight percent) | |
| Component | Preferred | More Preferred |
| (a) gelatin | 3–20 | 3–15 |
| (b) silver halide emulsion | 0–50 | 0–40 |
| (c) coupler dispersion | 0–40 | 0–30 |
| (d) compound of Formula A | 0.1–20 | 0.1–10 |

The thickening agent (i.e., a compound of Formula A) that produce high viscosity in gelatin-containing melts, usually has the following criteria.

They comprise molecules with large hydrophobic groups solubilized by one or more fully charged anionic groups such as —$SO_3^-$ groups or carboxy groups. As mentioned above, neither thickening agent nor any other component in the composition should contain —$SO_2^-$ groups.

The water solubility characteristics range from fully water soluble, to solubility of at least about 5% in a blend of water and about 5% to about 20% by weight of a water miscible organic solvent such as methanol, ethanol, propanol, isopropanol, acetone, methyl ethyl ketone, ethyl acetate, etc. at temperatures between 35° to 50° C. (Use of such water miscible solvent in the amount specified is referred to herein as "solvent assisted" or "solvent enhanced" or "solvent enhancement".)

The thickening agent is usually added to melts containing gelatin and other photographic components from a clear aqueous or a mixed solution, such that the temperature of the mixture of the solution and the gelatin solution is between 35° to 50° C.

Figure 2:
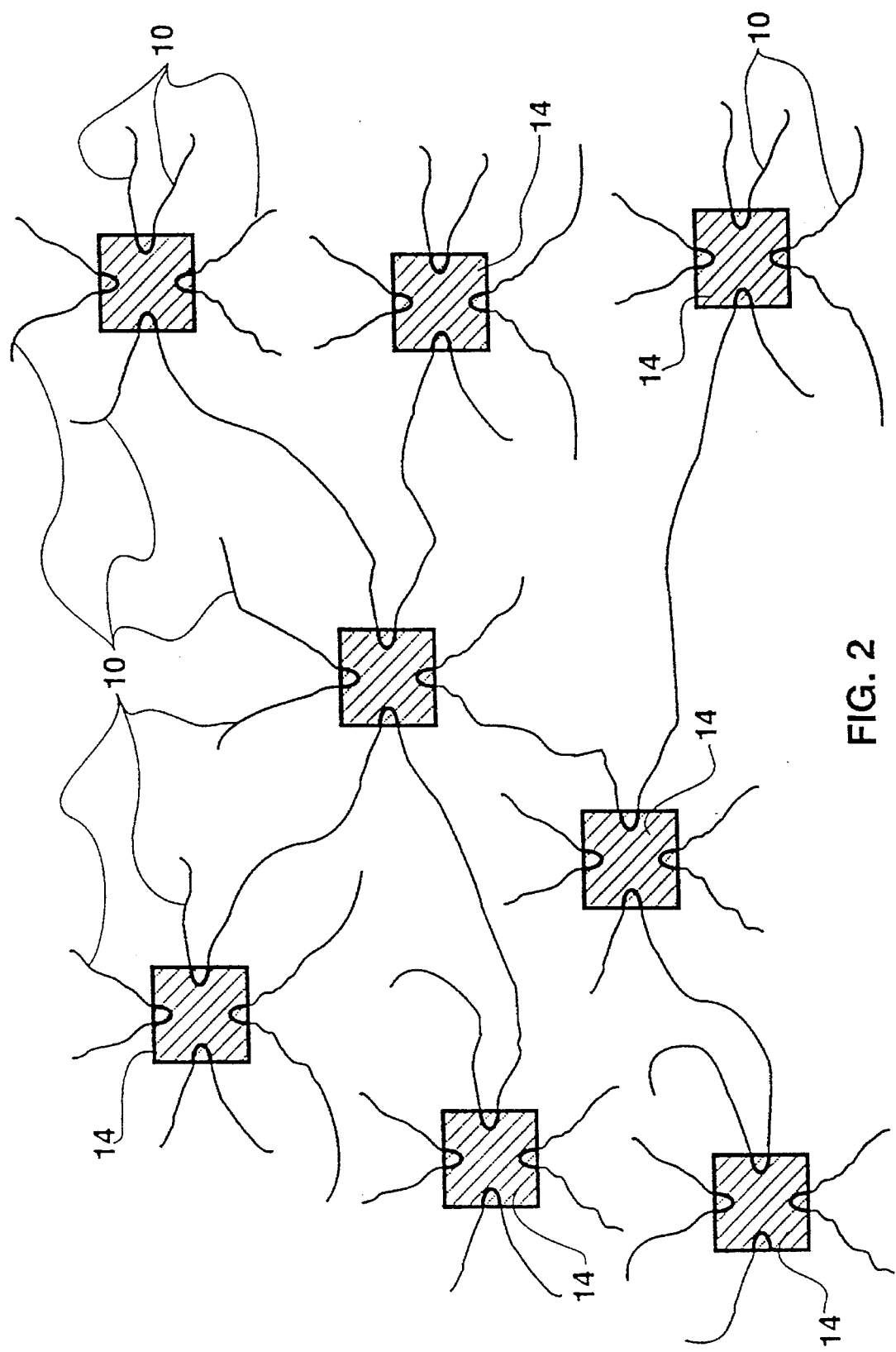
FIG. 2 illustrates attachment of multiple units of FIG. 1 to each other.

While not wishing to be bound by any theory, it is believed that there are a number of reasons why such photographic thickening agents produce higher melt viscosities when added to gelatin-containing photographic compositions. FIG. 1 shows that gelatin molecules 10 have hydrophobic segments 12 (marked by a heavy line). The hydrophobic segments 12 of a plurality of gelatin molecules can attach to the hydrophobic areas of the charged thickening agents 14, thereby effectively increasing the molecular weight of the gelatin in the melt. Attachment of multiples of such thickening agent 14/gelatin 10 units to each other (as shown in FIG. 2) can produce substantially higher viscosities.

Gelatin is polypeptide with pendant carboxyl and various amine groups. At any given pH, depending upon the pKa of the amine groups, the gelatin molecule has both positive and negative charges (cf. T. H. James, The Theory of the Photographic Process, 4th Ed., MacMillan, New York, 1977). As shown in configuration 4 of FIG. 3a, due to the partial neutralization of the various ionized groups, the gelatin molecule is fairly compactly coiled, especially so near the isoelectric point of the gelatin molecule. In configuration 4 of FIG. 3a, the hydrophobic sections of the gelatin molecule are marked with heavier lines designated by 2. Negatively charged smaller hydrophobic molecules, such as those of the thickening agents 14 in question, may individually bind to the hydrophobic sites of the gelatin molecule and render it highly charged. In such a case, due to charge repulsion, the gelatin molecule will acquire a highly expanded structure as shown in configuration 6 of FIG. 3b. This process of enhanced excluded volume will also lead to substantial enhancement of viscosity of the gelatin melt, and is an alternate mechanistic explanation for the viscosity enhancement process discussed earlier. It is to be understood that the effectiveness of the compounds added to photographic melts in accordance with this invention may be due undiscovered reasons.

The following examples are intended to be illustrative and not exhaustive illustrations of this invention. Parts and percentages are by weight unless otherwise specified.

PREPARATIVE EXAMPLE

A compound of structure No. 1, above, for use as a thickening agent for photographic compositions in accordance with this invention was prepared according to the following reaction:

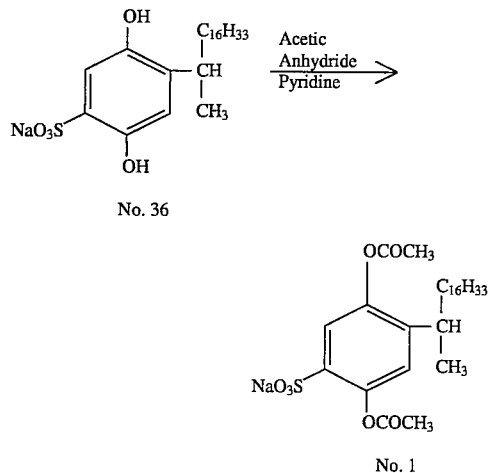

Acetic anhydride (25 mL) was added to a mixture of compound 36 in 25 mL of pyridine with stirring. The mixture was then heated at 80° C. for 16 hours. After cooling to room temperature the reaction mixture was diluted with acetone (100 mL) and the product compound No. 1 was isolated by filtration as a white solid, m.p. 223°–225° C. Yield was 7.9 g. Proton NMR and elemental analysis were consistent with the structure.

Compound 36 is an oxidized developer scavenger widely used in the photographic industry.

Compound 36 being an oxidized developer scavenger is not useful as a gelatin melt thickening agent as it produces photographic sensitometric changes. However, since the phenol groups are blocked in the compound 1, it is not expected to have any effect on photographic sensitometry.

MELT EXAMPLES 1 THROUGH 6

Photographic melts containing very low concentrations of photographic gelatin (deionized lime processed ossein) were prepared. Each composition contained 3.5% gelatin and compound 1 (prepared above) at levels between 0 and 20% by weight as indicated in Table 1. The pH of all the melts were adjusted to 7.0 using few drops of $10^{-3}$M NaOH solution.

Figure 4:
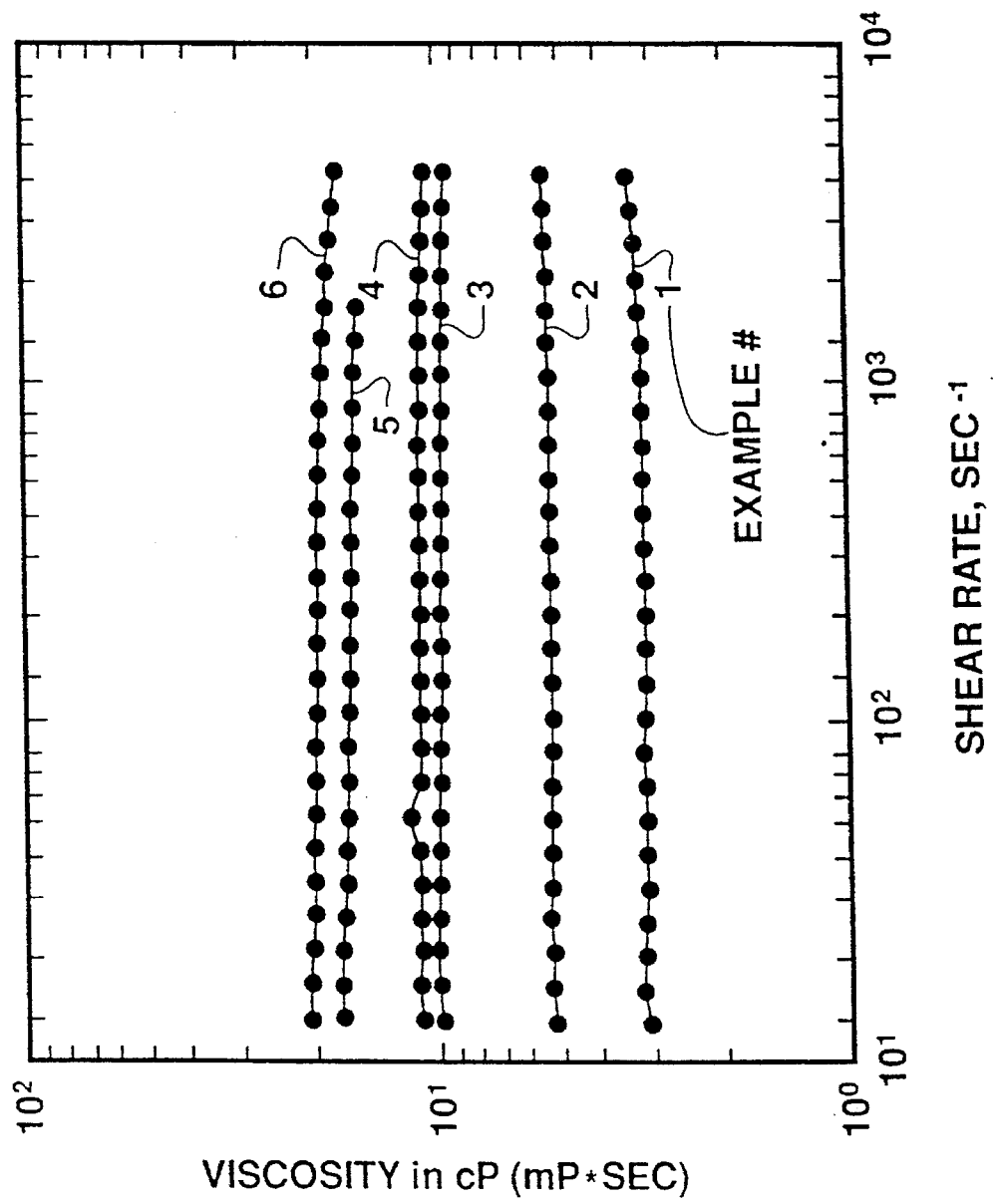
FIG. 4 depicts rheograms of melts of compositions of this invention as set forth in the examples below.

Rheograms of melt Examples 1 through 6 were measured using a Rheometrics rheogeneometer at 40° C. and are shown in FIG. 4. Rheograms of FIG. 4 depict the viscosities of these melts as a function of shear rate.

The gelatin melt of Example 1 with no additive of this invention, called the comparison example, has a very low viscosity of about 3 cP (mP*s) (at 100/sec shear rate) and it is virtually Newtonian as indicated by its virtual independence of shear rate. In Table I are listed viscosities of all the melt examples at 40° C. and a shear rate of 100/sec. The values of the slopes of the rheogram between 100 and 200/sec are also indicated in this table. The virtual zero slope of the rheogram of melt Example 1 is indicative of its Newtonian behavior.

TABLE I

Composition and Rheology of Aqueous Gelatin Melts of This Invention

| Example | Composition | | | | Rheology at 40° C. | |
|---|---|---|---|---|---|---|
| | % Gelatin | % Cmpd | % Water | pH | Viscosity n in cP or mP*s at 100/sec | Slope of Rheogram[1] of FIG. 4 |
| 1 (comparison) | 3.5 | 0.0 | 96.5 | 7.0 | 3.0 | 0.00 |
| 2 (invention) | 3.5 | 2.5 | 94.0 | 7.0 | 5.2 | 0.00 |
| 3 (invention) | 3.5 | 5.0 | 91.5 | 7.0 | 9.8 | −0.03 |
| 4 (invention) | 3.5 | 10.0 | 86.5 | 7.0 | 11.0 | −0.04 |
| 5 (invention) | 3.5 | 15.0 | 81.5 | 7.0 | 17.1 | −0.05 |
| 6 (invention) | 3.5 | 20.0 | 76.5 | 7.0 | 19.5 | −0.09 |

[1]Between shear rates of 100 and 200 $s^{-1}$.

Figure 5:
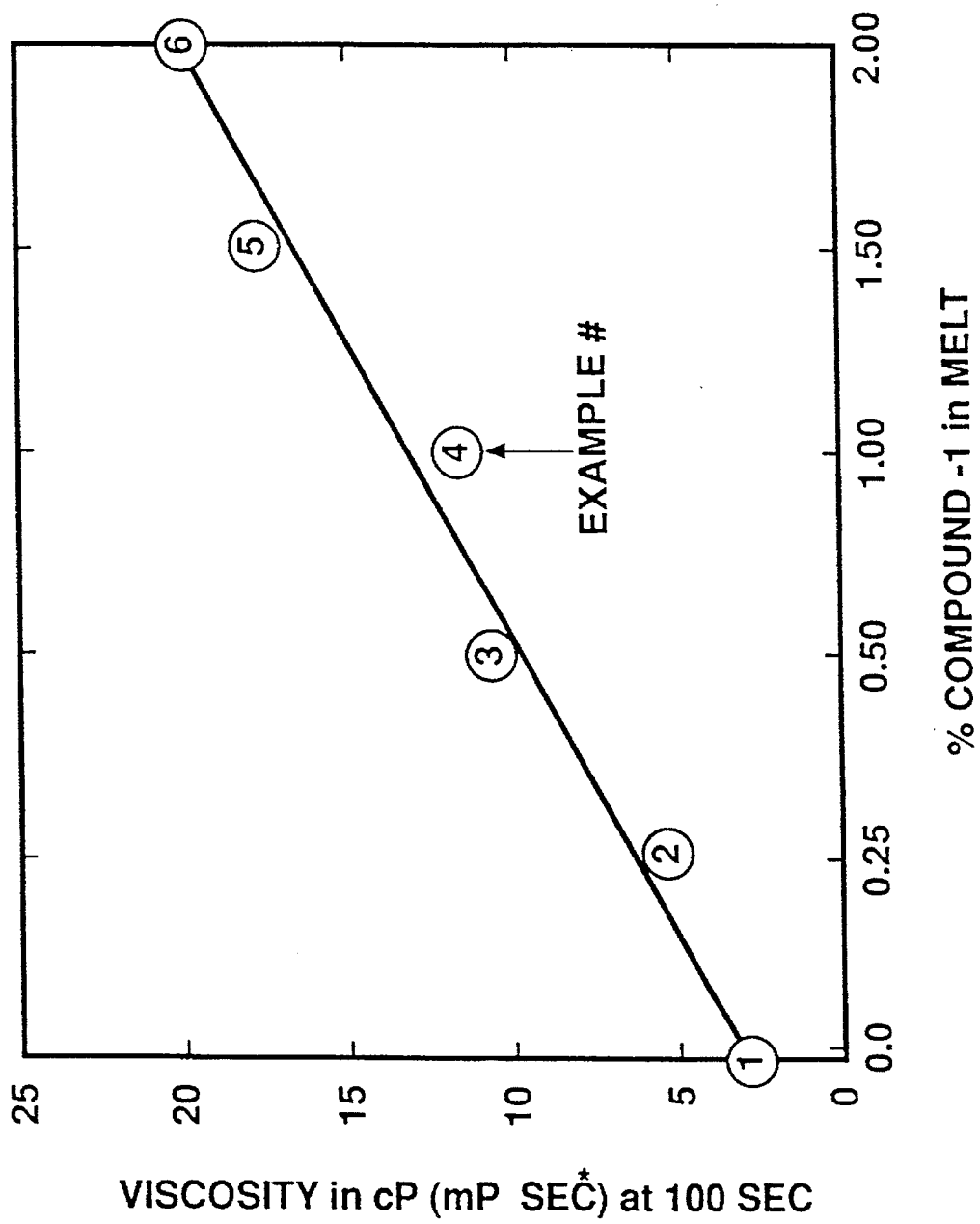
FIG. 5 is a graph setting forth the viscosity in the melt of compositions of this invention as set forth in the examples below.

It is seen in Table I and FIGS. 4 and 5 that increasing the concentration of the thickening agent of structure No. 1 causes a drastic increase of the viscosity of the prepared melt. At 20% concentration of compound 1 a viscosity of 19.5 cP (mP*sec) is reached. This is about a 600% increase of viscosity of a gelatin melt containing 3.5% gelatin, indicating the extreme gelatin thickening activity of the thickening agent.

It should be noted that all the melts containing compound 1 show virtually no shear rate dependence of the melt viscosities (FIG. 4 and Table I). This is an added advantage of the invention as the melt thickening advantage will be realizable even at very high coating speeds.

The invention has been described in detail with particular reference to preferred embodiments thereof, but it will be understood that variations and modifications can be affected within the spirit and scope of the invention.

What is claimed is:

1. A photographic composition comprising an aqueous medium containing gelatin present in an amount less than about 4% by weight, based on the weight of the composition, and a compound of the formula:

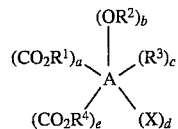

wherein:
A is an aromatic group;
X is $SO_3M$ or $CO_2M$,
M is H or an alkali metal, ammonium or pyridinium ion;
each $R^1$, $R^2$, and $R^3$ is independently a straight or branched chain alkyl group having 1 to 30 carbon atoms;
$R^4$ is H or a straight or branched chain alkyl group having 1 to 30 carbon atoms;
each of a, b, c and e is independently 0, 1, 2 or 3, with the proviso that a+b+c+e is at least 1; and
d is 1, 2, or 3;
with the further proviso that the sum of a+b+c+e is at least 2 when A is phenyl, X is $SO_3M$, d is 1 and any one of a, c, or e is 1; and wherein said composition would have a viscosity of less than 5 cP at a shear rate of 100 $sec^{-1}$ and a temperature of 40° C. in the absence of said compound, and said compound is present in said composition in an amount sufficient to raise the viscosity of said composition to above 5 cP at said shear rate and said temperature.

2. A photographic composition of claim 1 wherein said compound has the formula:

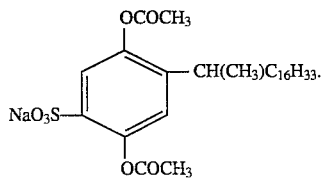

3. A photographic composition of claim 1, wherein said compound is present in an amount of about 0.1 to about 20% by weight, based on the weight of the composition.

4. A photographic composition of claim 1 which further comprises an emulsion of silver halide particles.

5. A photographic composition of claim 1, which further comprises dispersed coupler particles.

6. A multilayer photographic element comprising a support having on a surface thereof at least one layer formed from a photographic composition of claim 1.

7. A method of preparing a multilayer photographic element which comprises applying to a support a plurality of photographic layers, at least one of said layers being formed from a photographic composition of claim 1.

8. A photographic composition of claim 1 wherein A is phenyl; X is $SO_3M$; M is H, or a sodium, potassium, pyridium, or ammonium ion; $R^3$ is a straight or branched chain alkyl group having 1 to 30 carbon atoms; $R^4$ is a straight or branched chain alkyl group having 1 to 30 carbon atoms; d is 1, 2 or 3; c is 1; e is 2 or 3; and a and b are each 0.

9. A photographic composition of claim 1 wherein the compound is of the formula:

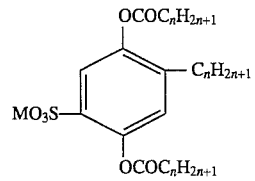

wherein M is H or an alkali metal, ammonium or pyridinium ion; and n is from 1 to about 18 for each $C_nH_{2n+1}$ group.

10. A photographic composition of claim 9, wherein the total number of alkyl carbon atoms in the $C_nH_{2n+1}$ groups of the compound is from about 8 to about 30.

11. A photographic composition of claim 1 wherein there is an absence of a compound containing one or more $—SO_2^-$ groups in the composition.

12. A photographic composition comprising an aqueous medium containing gelatin present in an amount less than about 4% by weight, based on the weight of the composition, and a compound selected from the group consisting of compounds of the formulas:

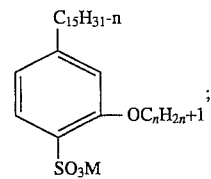

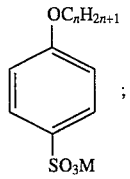

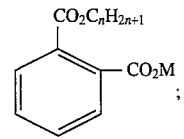

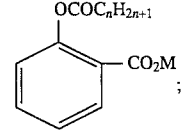

-continued and

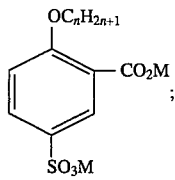

wherein M is H or an alkali metal, ammonium or pyridinium ion; n is from 1 to about 18; there is an absence of a compound containing one or more —$SO_2^-$ groups in the composition; and wherein said composition would have a viscosity of less than 5 cP at a shear rate of 100 $sec^{-1}$ and a temperature of 40° C. in the absence of said compound, and said compound is present in said composition in an amount sufficient to raise the viscosity of said composition to above 5 cP at said shear rate and said temperature.

13. A multilayer photographic element comprising a support having on a surface thereof at least one layer formed from a photographic composition of claim 12.

14. A method of preparing a multilayer photographic element which comprises applying to a support a plurality of photographic layers, at least one of said layers being formed from a photographic composition of claim 12.

15. A photographic composition of claim 12, wherein the total number of alkyl carbon atoms in said compound is from about 8 to about 30.

16. A method of thickening a photographic composition comprising an aqueous medium containing gelatin present in an amount less than about 4% by weight, based on the weight of the composition, from a viscosity of less than 5 cP at a shear rate of 100 $sec^{-1}$ and a temperature of 40° C. to a viscosity above 5 cP at said shear rate and said temperature, which method comprises adding thereto in an amount sufficient to raise the viscosity of said composition to a level above 5 cP a compound of the formula:

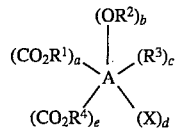

wherein:

A is an aromatic group;

X is $SO_3M$ or $CO_2M$,

M is H or an alkali metal, ammonium or pyridinium ion;

each $R^1$, $R^2$, and $R^3$ is independently a straight or branched chain alkyl group having 1 to 30 carbon atoms;

$R^4$ is H or a straight or branched chain alkyl group having 1 to 30 carbon atoms;

each of a, b, c and e is independently 0, 1, 2 or 3, with the proviso that a+b+c+e is at least 1; and d is 1, 2, or 3;

with the further proviso that the sum of a+b+c+e is at least 2 when A is phenyl, X is $SO_3M$, d is 1 and any one of a, c, or e is 1.

17. A method of claim 16 wherein A is phenyl, X is $SO_3M$, M is H, or a sodium, potassium, pyridium, or ammonium ion, $R^3$ is a straight or branched chain alkyl group having 1 to 30 carbon atoms, $R^4$ is a straight or branched chain alkyl group having 1 to 30 carbon atoms, d is 1, 2 or 3, c is 1, e is 2 or 3 and a and b are each 0.

18. A method of claim 16 wherein there is an absence of a compound containing one or more —$SO_2^-$ groups in the composition.

* * * * *